United States Patent
Stewart et al.

(10) Patent No.: US 10,696,778 B1
(45) Date of Patent: Jun. 30, 2020

(54) METHODS OF MAKING POLYMERS USING ISOSORBIDE

(71) Applicant: Novol, Inc., San Leandro, CA (US)

(72) Inventors: Ray F. Stewart, Redwood City, CA (US); Monica Bhatia, San Leandro, CA (US); Jagdish Jethmalani, San Leandro, CA (US); Sanjiban Chakraborty, San Leandro, CA (US)

(73) Assignee: NOVOL, INC., San Leandro, CA (US)

( * ) Notice: Subject to any disclaimer, the term of this patent is extended or adjusted under 35 U.S.C. 154(b) by 75 days.

(21) Appl. No.: 15/880,298

(22) Filed: Jan. 25, 2018

Related U.S. Application Data (60) Provisional application No. 62/450,629, filed on Jan. 26, 2017.

(51) Int. Cl.
| | | |
|---|---|---|
| *C08G 18/32* | (2006.01) | |
| *C08G 18/75* | (2006.01) | |
| *C08L 75/04* | (2006.01) | |
| *C07D 497/04* | (2006.01) | |
| *C07D 493/04* | (2006.01) | |
| *G01N 21/35* | (2014.01) | |
| *G01N 25/48* | (2006.01) | |
| *G01N 21/41* | (2006.01) | |

(52) U.S. Cl.
CPC ....... *C08G 18/3218* (2013.01); *C07D 493/04* (2013.01); *C07D 497/04* (2013.01); *C08G 18/751* (2013.01); *C08L 75/04* (2013.01); *G01N 21/41* (2013.01); *G01N 25/4866* (2013.01); *G01N 2021/3595* (2013.01)

(58) Field of Classification Search
CPC .............. C08G 18/3218; C08G 18/751; C07D 493/04; C07D 497/04; C08L 75/04; G01N 21/41; G01N 25/4866; G01N 2021/3595

See application file for complete search history.

(56) References Cited

U.S. PATENT DOCUMENTS

| | | | |
|---|---|---|---|
| 6,830,332 B2 | 12/2004 | Piers et al. | |
| 8,865,855 B2 | 10/2014 | Fuji et al. | |
| 2005/0143549 A1* | 6/2005 | Schijndel | C08G 18/10 528/44 |
| 2010/0136347 A1* | 6/2010 | Simons | B32B 27/32 428/423.7 |
| 2013/0267624 A1* | 10/2013 | Chopra | C07D 493/04 522/75 |
| 2016/0282515 A1* | 9/2016 | Tsukada | B29D 11/00403 |
| 2017/0335055 A1* | 11/2017 | Jacquel | C08K 3/22 |

OTHER PUBLICATIONS

New Bio-based Engineering Plastic "DURABIO™" | Products | Mitsubishi Chemical Corporation, retrieved from the internet May 3, 2017(https://www.m-chemical.co.jp/en/products/departments/mcc/sustainable/product/1201026_7964.html), 5 pages.

* cited by examiner

*Primary Examiner* — Rabon A Sergent
(74) *Attorney, Agent, or Firm* — Duane Morris LLP (57) ABSTRACT

The present invention is based, in part, on the discovery that the polymeric materials described herein produce polyurethane copolymers with advantageous optical properties. In particular embodiments, polyurethane copolymers comprise repeating units of isosorbide and a difunctional linker where the difunctional linkers can be diisocyanate, dithiocyanate, dicarboxylic acid, and other monomers. Some of the advantageous optical properties of these polymeric materials include a refractive index of about 1.5 and an Abbe value of at least about 50. Also described are methods for producing these polyurethane copolymers.

13 Claims, 2 Drawing Sheets

METHODS OF MAKING POLYMERS USING ISOSORBIDE

CROSS-REFERENCES TO RELATED APPLICATIONS

The present application claims the benefit of U.S. Provisional Patent Application No. 62/450,629 filed Jan. 26, 2017, the full disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

None

BACKGROUND OF THE INVENTION

Polymeric materials are used in an extremely wide range of products. A category of polymeric materials having demanding requirements are polymeric materials used for optical applications. Such applications require very high light transmittance, very low levels of haze and good thermal and mechanical stability.

Traditional transparent polymers such acrylic, styrenic, and polycarbonate have been used in making optical lenses, eye glasses, head light covers, etc. They can be readily processed by injection molding. In other cases, a simple blank or block of the polymer may be machined to produce the optical product. Other polymers are used for lenses wherein monomers or pre-polymers are placed into a mold or cavity and polymerized directly to a shape of interest, for example an ophthalmic lens, component for a microscope or contact lens.

The optical properties of materials can be determined by measuring the refractive index and Abbe value. When light moves from a material of one refractive index to a material with a different refractive index it is bent, and the amount of bending is determined by the difference between the refractive index of the two materials. Higher refractive index materials are therefore useful in applications such as optical lenses, which achieve a larger amount of light refraction with a thinner lens than materials when compared to lenses with a lower refractive index.

If the index of refraction varies significantly with wavelength in the visible region, a lens may suffer chromatic aberration. A lens with chromatic aberration produces distorted images that lack clarity.

Current materials used to make polyurethane copolymers with high optical properties have many drawbacks including the use of highly reactive and toxic monomers, high cost of component chemicals and difficulty in controlling optical properties such as chromatic aberration, refractive index, and Abbe value.

As such, there is a need in the art for a novel and efficient methods for producing optical lenses with advantageous optical properties. The present disclosure satisfies this need and provides other advantages as well.

BRIEF SUMMARY OF THE INVENTION

In one aspect, the present invention provides a polyurethane copolymer comprising a repeating unit of Formula I:

(I)

wherein:
ISO in each repeating unit is independently selected from isosorbide or a stereoisomer thereof; and
X in each repeating unit is an independently selected difunctional linker,
wherein X in at least one repeating unit is a difunctional isocyanate linker, and
wherein the polyurethane copolymer has a refractive index of at least about 1.5 and an Abbe value of at least about 50.

In some embodiments, the stereoisomer of isosorbide is selected from the group consisting of isomannide and isoidide.

In some embodiments, the difunctional isocyanate linker is selected from the group consisting of a diisocyanate and a diisothiocyanate.

In some embodiments, the diisocyanate is selected from the group consisting of 4, 4'-methylenebis(cyclohexylisocyanate) (H12MDI), methylenebis(phenylisocyanate), hexamethylene diisocyanate, isophorone diisocyanate, cyclohexane diisocyanate, butane diisocyanate, and 1,3-bis(isocyanatomethyl) cyclohexane.

In some embodiments, the diisothiocyanate is selected from the group consisting of 4, 4'-methylenebis(cyclohexylisothiocyanate), methylenebis(phenylisothiocyanate), hexamethylene diisothiocyanate, isophorone diisothiocyanate, cyclohexane diisothiocyanate, butane diisothiocyanate, and 1,3-bis(isothiocyanatomethyl) cyclohexane.

In some embodiments, the difunctional linker is selected from the group consisting of a dicarboxylic acid, a dithiocarboxylic acid, a carbonate, a thiocarbonate, and a difunctional compound comprising carboxylic acid and thiocarboxylic acid functional groups.

In some embodiments, the dicarboxylic acid is selected from the group consisting of succinic acid, 3,3'-disulfanediyldipropanoic acid, 2,2'-disulfanediyldiethanoic acid, and 4,4'-disulfanediyldibutanoic acid.

In some embodiments, the dithiocarboxylic acid is selected from the group consisting of succinthioic acid, 3,3'-disulfanediyldipropanthioic acid, 2,2'-di sulfanediyldiethanthioic acid, and 4,4'-disulfanediyldibutanthioic acid.

In some embodiments, the difunctional compound is selected from the group consisting of 4-((3-thiocarboxypropyl)disulfanyl)butanoic acid, 3-((2-thiocarboxyethyl)disulfanyl) propionic acid, 2-((thiocarboxymethyl)disulfanyl) acetic acid, and 4-hydroxy-4-thioxobutanoic acid.

In some embodiments, the polyurethane copolymer has a light transmittance of at least about 80%. In some embodiments, the polyurethane copolymer has a yellow index of lower than about 10.

In another aspect, the present invention provides an isosorbide adduct of Formula II (II)

wherein:
ISO is independently selected from isosorbide or a stereoisomer thereof; and
Y is a difunctional linker.

In some embodiments, the stereoisomer is selected from the group consisting of isomannide and isoidide.

In some embodiments, the difunctional linker is selected from the group consisting of a dicarboxylic acid, a dithiocarboxylic acid, a carbonate, a thiocarbonate, and a difunctional compound comprising carboxylic acid and thiocarboxylic acid functional groups.

In some embodiments, the dicarboxylic acid is selected from the group consisting of succinic acid, 3,3'-disulfanediyldipropanoic acid, 2,2'-di sulfanediyldiethanoic acid, 4,4'-disulfanediyldibutanoic acid, octanedioic acid, and hexanedioic acid.

In some embodiments, the dithiocarboxylic acid is selected from the group consisting of succinthioic acid, 3,3'-disulfanediyldipropanthioic acid, 2,2'-disulfanediyldiethanthioic acid, and 4,4'-disulfanediyldibutanthioic acid.

In some embodiments, the difunctional compound is selected from the group consisting of 4-((3-thiocarboxypropyl)disulfanyl)butanoic acid, 3-((2-thiocarboxyethyl)disulfanyl) propionic acid, 2-((thiocarboxymethyl)disulfanyl) acetic acid, and 4-hydroxy-4-thioxobutanoic acid.

In another aspect, the present invention provides a polyurethane copolymer comprising
one or more isosorbide adducts of Formula II; and
one or more difunctional isocyanate linkers.

In some embodiments, the difunctional isocyanate linker is selected from the group consisting of a diisocyanate, a diisothiocyanate, and combinations thereof.

In some embodiments, the diisocyanate is selected from the group consisting of 4, 4'-methylenebis(cyclohexylisocyanate) (H12MDI), methylenebis(phenylisocyanate), hexamethylene diisocyanate, isophorone diisocyanate, cyclohexane diisocyanate, butane diisocyanate, 1,3-bis(isocyanatomethyl) cyclohexane, and combinations thereof.

In some embodiments, the diisothiocyanate is selected from the group consisting of 4, 4'-methylenebis(cyclohexylisothiocyanate), methylenebis(phenylisothiocyanate), hexamethylene diisothiocyanate, isophorone diisothiocyanate, cyclohexane diisothiocyanate, butane diisothiocyanate, 1,3-bis(isothiocyanatomethyl) cyclohexane, and combinations thereof.

In some embodiments, the polyurethane copolymer has a refractive index of at least about 1.5. In some embodiments, the polyurethane copolymer has a light transmittance of at least about 80%. In some embodiments, the polyurethane copolymer has a yellow index of lower than about 10.

In another aspect, the present invention provides a method for preparing a polyurethane copolymer with an isosorbide adduct comprising
(a) combining isosorbide or a stereoisomer thereof with a difunctional linker to form a first reaction mixture;
(b) reacting the first reaction mixture under conditions to form an isosorbide adduct;
(c) admixing a difunctional isocyanate linker to the isosorbide adduct to form a second reaction mixture; and
(d) reacting the second reaction mixture under conditions to form a polyurethane copolymer with the isosorbide adduct.

In some embodiments, the method includes a catalyst in the second reaction mixture.

In some embodiments, the method includes isolating the isosorbide adduct from the first reaction mixture.

In some embodiments, the stereoisomer of isosorbide is selected from the group consisting of isomannide and isoidide.

In some embodiments, the difunctional linker is selected from the group consisting of a dicarboxylic acid, a dithiocarboxylic acid, a diester, a cyclic anhydride, carbonate, a thiocarbonate, and a difunctional compound comprising carboxylic acid and thiocarboxylic acid functional groups.

In some embodiments, the difunctional cyanate linker is selected from the group consisting of a diisocyanate, a diisothiocyanate, and combinations thereof.

Other objects, features, and advantages of the present invention will be apparent to one of skill in the art from the following detailed description and figures.

DETAILED DESCRIPTION OF THE INVENTION

I. Introduction

The present invention is based, in part, on the discovery that the polymeric materials described herein produce polyurethane copolymers with advantageous optical properties. In particular embodiments, polyurethane copolymers comprise repeating units of isosorbide and a difunctional linker where the difunctional linkers can be diisocyanate, dithiocyanate, dicarboxylic acid, and other monomers. Some of the advantageous optical properties of these polymeric materials include a refractive index of about 1.5 and an Abbe value of at least about 50. Also described are methods for producing these polyurethane copolymers.

The polymers described herein can be used to make any kind of plastic product. In particular embodiments, the polymers can be used to make optical products such as ophthalmic lenses. In some embodiments, the polymers may be useful components in light guides, fiber optics, adhesives, films or sheets. In some embodiments, the polymers of the present invention may be useful for making sunglasses, magnifying glasses, concentrators for solar cells, and microscopic lenses.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X.

Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

The term "copolymer" refers to a large molecule consisting of linked monomer units of two or more compounds. In the present disclosure, the term copolymer may refer to polymers with 2, 3, 4, 5, 6, 7, 8, 9, 10, or more monomeric units. For instance, the term copolymer may refer to a polymer with two monomeric units (e.g. isosorbide and 4,4'-methylenebis(cyclohexylisocyanate)) as well as a polymer with three monomeric units (e.g. isosorbide, succinic acid, and 4,4'-methylenebis(cyclohexylisocyanate)).

The term "thiocarboxylic acid" refers to carboxylic acid functional groups that contain at least one oxygen substituted with a sulfur. Thiocarboxylic acids in the present disclosure may be the S-acid, meaning the sulfur substitution is at the alcohol position of the carboxylic acid, the O-acid, meaning the sulfur substitution is at the oxo position of the carboxylic acid, or substituted at both positions. For clarity, the structures below illustrate the different forms of thiocarboxlylic acids. Dithiocarboxylic acids refer to compounds with two thiocarboxylic acid groups.

S-acid      O-acid

III. Description of the Embodiments

A. Isosorbide Polyurethane Copolymers

The isosorbide polyurethane copolymers described herein are useful in the manufacture of transparent solid materials with advantageous optical properties including high refractive index and Abbe value.

In one aspect, the present invention provides a polyurethane copolymer comprising a repeating unit of Formula I:

(I)

wherein:
ISO in each repeating unit is independently selected from isosorbide or a stereoisomer thereof; and
X in each repeating unit is an independently selected difunctional linker,
wherein X in at least one repeating unit is a difunctional isocyanate linker, and
wherein the polyurethane copolymer has a refractive index of at least about 1.5 and an Abbe value of at least about 50.

Isosorbide is a bicyclic diol derivative of sorbitol. The chemical structure of isosorbide is shown below.

The ISO repeating unit shown in Formula I may be isosorbide or any stereoisomer thereof including isoidide and isomannide. These two isomers differ from isosorbide in the spatial arrangement of the OH bonds with respect to the bicyclic five membered rings. Each repeating unit may have a different stereoisomer of isosorbide. Thus, the resulting polymer may possess a mixture of isosorbide and its stereoisomers.

In each polymer described herein, at least one X is a difunctional isocyanate linker. Such cyanate linkers can be either diisocyanates or diisothiocyanates. The generic structures of a isocyanate and an isothiocyanate are shown below.

isocyanate      isothiocyanate

Diisocyanates and diisothiocyanates are molecules that contain two of these functionalities on one molecule. Each isocyanate and isothiocyanate is typically attached to a different carbon atom within the molecule. In some embodiments, the difunctional linker contains an isocyanate functionality and a isothiocyanate functionality. In some embodiments both diisocyanates or diisothiocyanates are used.

In some embodiments, the diisocyanate is 4, 4'-methylenebis(cyclohexylisocyanate) (H12MDI), methylenebis(phenylisocyanate), hexamethylene diisocyanate, isophorone diisocyanate, cyclohexane diisocyanate, butane diisocyanate, 1,3-bis(isocyanatomethyl) cyclohexane, or combinations thereof. In some embodiments, hexamethylene diisocyanate is CAS No. 822-06-0. In some embodiments, isophorone diisocyanate is CAS No. 4098-71-9. In some embodiments, cyclohexane diisocyanate is CAS No. 7517-76-2. In some embodiments, butane diisocyanate is CAS No. 4538-37-8. In some embodiments, 1,3-bis(isocyanatomethyl) cyclohexane is CAS No. 38661-72-2.

In some embodiments, the diisothiocyanate is 4, 4'-methylenebis (cyclohexylisothiocyanate), methylenebis(phenylisothiocyanate), hexamethylene diisothiocyanate, isophorone diisothiocyanate, cyclohexane diisothiocyanate, butane diisothiocyanate, 1,3-bis(isothiocyanatomethyl) cyclohexane, or combinations thereof.

In some embodiments, the difunctional cyanate linker comprises an isocyanate and an isothiocyanate.

The difunctional linker shown as X in Formula I can also include a dicarboxylic acid, a dithiocarboxylic acid, a carbonate, a thiocarbonate and a difunctional compound comprising carboxylic acid, thiocarboxylic acid functional groups, and combinations thereof.

In some embodiments, the dicarboxylic acids, dithiocarboxylic acids, and difunctional compounds comprising a carboxylic acid and thiocarboxylic acid functional groups described herein are linear molecules lacking cyclic or aromatic components.

In some embodiments, the dicarboxylic acids, dithiocarboxylic acids, and difunctional compounds comprising a carboxylic acid and a thiocarboxylic acid functional groups of Formula I are linear molecules with each functional group of the difunctional groups separated by 6 or fewer carbons. In some embodiments, the difunctional linker includes a disulfide bond. In some embodiments, the difunctional linker is an unbranched linear compound. In some embodiments, the difunctional linker contains 4 or fewer carbon atoms between functional groups. In certain embodiments, the separation between difunctional linkers is not greater than 5 carbon atoms. For example, in some embodiments, a difunctional linker used in the copolymers described herein is 3,3'-disulfanediyldipropanoic acid, the structure of which is shown below.

3,3'-disulfanediyldipropanoic acid

In some embodiments, the dicarboxylic acids, dithiocarboxylic acids, and difunctional compounds comprising carboxylic acid, thiocarboxylic acid functional groups described herein are unbranched linear molecules with functional groups on the terminal carbon of the chain.

The identity and mole percentage of the difunctional linkers used depends on the desired physical and optical properties of the polymer. For example, when a more rigid polymer is desired a difunctional linker such as 3,3'-disulfanediyldipropanoic acid can be incorporated into the polymer.

In some embodiments, the dicarboxylic acid used as a difunctional linker in the above described polymers is succinic acid, 3,3'-disulfanediyldipropanoic acid, 2,2'-disulfanediyldiethanoic acid, and 4,4'-disulfanediyldibutanoic acid, or combinations thereof.

In some embodiments, the dithiocarboxylic acid used as a difunctional linker in the above described polymers is succinthioic acid, 3,3'-disulfanediyldipropanthioic acid, 2,2'-disulfanediyldiethanthioic acid, 4,4'-disulfanediyldibutanthioic acid, or combinations thereof. In preferred embodiments, the dithiocarboxylic acid is the O-acid.

In some embodiments, the difunctional compound comprising a carboxylic acid and a thiocarboxylic acid used as a difunctional linker in the above described polymers is 4-((3-thiocarboxypropyl)disulfanyl)butanoic acid, 3-((2-thiocarboxyethyl)disulfanyl)propionic acid, 2-((thiocarboxymethyl)disulfanyl)acetic acid, 4-hydroxy-4-thioxobutanoic acid, or combinations thereof.

The polymers described herein may have a weight average molecular weight (Mw) as determined by gel permeation chromatography of about 10,000 to about 700,000, about 25,000 to about 500,000, about 100,000 to about 500,000, or about 200,000 to about 500,000.

The polymers described herein may have a refractive index of at least about 1.45, 1.50, 1.52, 1.54, 1.56, 1.58, 1.60, 1.62, 1.64, 1.66, 1.68, 1.70, 1.72, 1.74, 1.76, 1.78, or 1.80 as determined by an Abbe refractometer or similar device.

The polymers described herein may have light transmittance of at least 70, 75, 80, 85, 90, or 95 percent, or higher. The transmittance of the polymers described herein is determined by measuring the visible light transmittance in a spectrophotometer and averaging the percent transmittance measured at 420 nm, 480 nm, 520 nm, 580 nm, and 660 nm.

The polymers described herein may have a yellow index (YI) lower than about 20, 15, 14, 13, 12, 11, 10, 9, 8, 7, 6, or 5 as determined by a HunterLab color measurement instrument using ATSM method E313.

The polymers described herein may have an Abbe value of at least about 40, 45, 50, 55, 60, 65, 70, 75, or 80.

The Abbe value (VD) of a material is defined as $$V_D = \frac{n_D - 1}{n_F - n_C},$$

where $n_D$, $n_F$ and $n_C$ are the refractive indices of the material at the wavelengths of the Fraunhofer D-, F- and C-spectral lines (589.3 nm, 486.1 nm and 656.3 nm respectively).

The polymers described herein may have a glass transition temperature (Tg) as measured by differential scanning calorimeter (DSC) of about 80° C. to about 300° C., of about 100° C. to about 275° C., of about 125° C. to about 250° C., of about 150° C. to about 225° C., or of about 175° C. to about 200° C.

The polymers described herein may have an elastic modulus of about 1.0 GPa to about 4 GPa, 2.0 GPa to about 6.0 GPa or about 3.0 GPa to about 5.0 GPa, as determined by ASTM D 638.

The polymers described herein may have a hardness of about 100 MPa to about 200 MPa, 100 MPa to about 350 MPa, about 200 MPa to about 325 MPa, about 225 MPa to about 300 MPa, or about 250 MPa to about 275 MPa.

In preferred embodiments, the polymers described herein optimize one or more of the above referenced optical properties including having a high refractive index, Abbe value, and transmittance and having a low yellowing index, while minimizing chromatic aberration.

Figure 1:
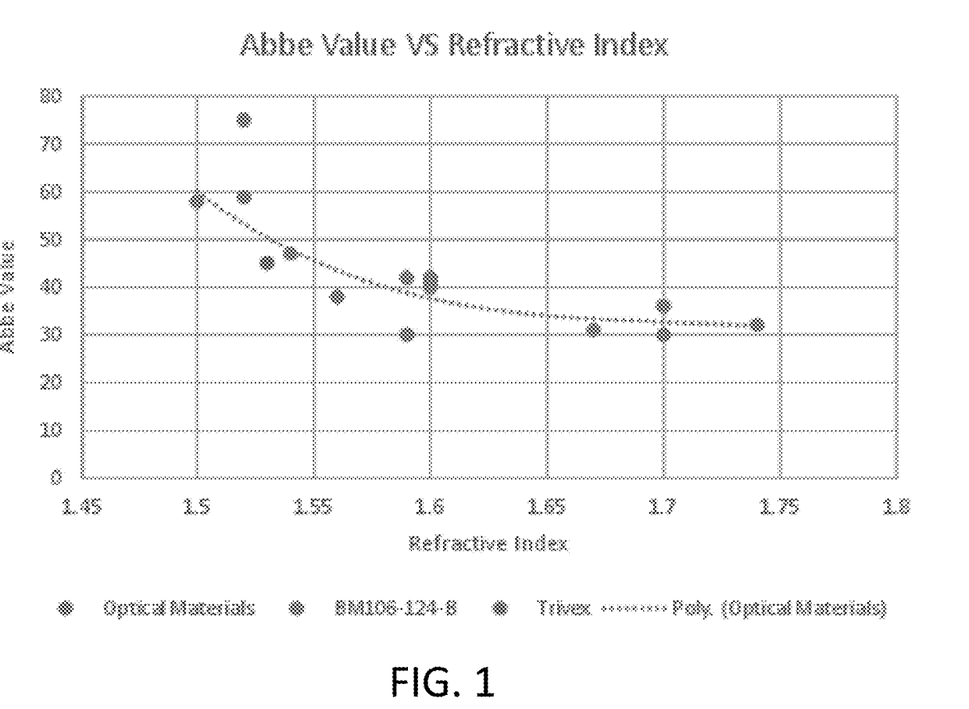
FIG. 1 shows a plot of Abbe value vs. refractive index of standard optical materials. The plot includes data points of an ophthalmic lens used today, and of a polymer in accordance with an embodiment of the present invention.

FIG. 1 shows a plot of Abbe value vs. refractive index of standard optical materials. The plot includes data points of an ophthalmic lens used today, and a polymer in accordance with an embodiment of the present invention.

B. Isosorbide Adducts

Provided herein are isosorbide adducts that may be used in the synthesis of polyurethane copolymers with high refractive index and Abbe value. The isosorbide adducts of the present invention include isosorbide adducts according to Formula II:

wherein:
ISO is independently selected from isosorbide or a stereoisomer thereof; and
Y is a difunctional linker.

The ISO in the adduct of Formula II may be isosorbide or any stereoisomer thereof including isoidide and isomannide. In some embodiments, only a single isosorbide stereoisomer is present in the adduct. In some embodiments, a mixture of one or more isosorbide stereoisomers are present in the adduct.

The exocyclic alcohol functional groups of the ISO groups of Formula II are shown as OH.

The difunctional linker can include a dicarboxylic acid, a dithiocarboxylic acid, a carbonate, a thiocarbonate, and a difunctional compound comprising carboxylic acid thiocarboxylic acid functional groups.

In some embodiments, the dicarboxylic acids, dithiocarboxylic acids, and difunctional compounds comprising a carboxylic acid and a thiocarboxylic acid functional groups of Formula II are linear molecules with each functional group of the difunctional groups separated by 6 or fewer carbons. In some embodiments, these compounds contain a disulfide bond. In some embodiments, these compounds are unbranched linear compounds. In some embodiments, these compounds contain 4 or fewer carbon atoms between functional groups.

In some embodiments, the dicarboxylic acids, dithiocarboxylic acids, and difunctional compounds comprising carboxylic acid, thiocarboxylic acid functional groups described herein are unbranched linear molecules with functional groups on the terminal carbon of the chain.

In some embodiments, the dicarboxylic acid used as a difunctional linker in the above described polymers is succinic acid, 3,3'-disulfanediyldipropanoic acid, 2,2'-disulfanediyldiethanoic acid, and 4,4'-disulfanediyldibutanoic acid, or combinations thereof.

In some embodiments, the dithiocarboxylic acid used as a difunctional linker in the above described polymers is succinthioic acid, 3,3'-disulfanediyldipropanthioic acid, 2,2'-disulfanediyldiethanthioic acid, 4,4'-disulfanediyldibutanthioic acid, or combinations thereof. In preferred embodiments, the dithiocarboxylic acid is the O-acid.

In some embodiments, the difunctional compound comprising a carboxylic acid and a thiocarboxylic acid used as a difunctional linker in the above described polymers is 4-((3-thiocarboxypropyl)disulfanyl)butanoic acid, 3-((2-thiocarboxyethyl)disulfanyl)propionic acid, 2-((thiocarboxymethyl)disulfanyl)acetic acid, 4-hydroxy-4-thioxobutanoic acid, or combinations thereof.

In some embodiments, the isosorbide adducts of the present invention include isosorbide adducts according to Formula III:

(III)

wherein ISO and Y are as defined in Formula II and n can be any range as defined below.

The value of n in the isosorbide adduct of Formula III can range from about 1 to 3,000, 1 to 2,000, 1 to 1,000, 1 to 500, 1 to 400, 1 to 300, 1 to 200, 1 to 100, 1 to 50, or 1 to 20. In some embodiments, the value of n in the isosorbide adduct of Formula III can include 1, 2, 3, 4, 5, 6, 7, 7, 8, 9, 10, 11, 12, 13, 14, 15, 16, 17, 18, 19, 20, 21, 22, 23, 24, 25, 26, 27, 28, 29, 30, or more.

In some aspects, the present invention includes a polyurethane copolymer including one or more isosorbide adducts of Formula II and/or Formula III and one or more difunctional isocyanate linkers. In the described polymer, the difunctional isocyanate linkers connect the adducts of Formula II and/or Formula III (e.g. the polymer composition is A-B-A-B where A is a compound of formula II or Formula III and B is a difunctional cyanate linker).

In some embodiments, the diisocyanate is 4, 4'-methylenebis(cyclohexylisocyanate) (H12MDI), methylenebis(phenylisocyanate), hexamethylene diisocyanate, isophorone diisocyanate, cyclohexane diisocyanate, butane diisocyanate, 1,3-bis(isocyanatomethyl) cyclohexane, or combinations thereof.

In some embodiments, the diisothiocyanate is 4, 4'-methylenebis (cyclohexylisothiocyanate), methylenebis(phenylisothiocyanate), hexamethylene diisothiocyanate, isophorone diisothiocyanate, cyclohexane diisothiocyanate, butane diisothiocyanate, 1,3-bis(isothiocyanatomethyl) cyclohexane, or combinations thereof.

In some embodiments, the difunctional isocyanate linker comprises an isocyanate and an isothiocyanate.

In some embodiments, the polyurethane copolymer including an isosorbide adduct of Formula II and/or Formula III further comprises isosorbide or a stereoisomer thereof. That is to say, the monomeric units in this polymer include one or more adducts of Formula II and/or one or more adducts of Formula III, isosorbide or stereoisomers thereof, and one or more diisocyanate linkers. The diisocyanates are linkers that connect the adducts of Formula II and/or Formula III and isosorbide or stereoisomers thereof.

The polyurethane copolymer including isosorbide adducts of Formula II and/or Formula III may comprise any of the properties described in the previous section including average molecular weight, refractive index, percent transmittance, yellow index, Abbe value, glass transition temperature, elastic modulus, and hardness.

In some embodiments, the polyurethane copolymer including an isosorbide adduct of Formula II and/or Formula III and one or more difunctional cyanate linkers may comprise one or more isosorbide adducts of Formula III with different values of n.

In preferred embodiments, the polymers described herein optimize one or more of the above referenced optical properties including having a high refractive index, Abbe value, and light transmittance and having a low yellowing index, while minimizing chromatic aberration.

In some embodiments, two or more isosorbide adducts may be added to the second reaction mixture. In embodiments with two or more isosorbide adducts, the order of isosorbide adducts in the resulting copolymer may be regular (e.g. when two isosorbide adducts are used the order can be I-O-I-O-I-O-I-O where I represents one adduct, O represents the second adduct, and the '-' represents the difunctional isocyanate linker. The order of adducts in the copolymer may be arranged in a repeating sequence (e.g. a periodic copolymer having the formula: (I-O-I-O-O-I-I-I-I-O-O-O)$_n$) where n is the number of repetitions). The order of adducts in the copolymer may be a statistical copolymer in which the sequence of monomer residues follows a statistical rule. For example, if the probability of finding a given type monomer residue at a particular point in the chain is equal to the mole fraction of that monomer residue in the chain, then the polymer may be referred to as a truly random copolymer. The regular, repeating, and statistical ordering possibilities described herein are also possible in copolymers with three or more adducts.

C. Methods of Synthesis

Provided herein is a method of making isosorbide-containing polymers. The method centers on mixing isosorbide and stereoisomers thereof with one or more difunctional compounds and subjecting those compounds to polymerization conditions whereby structural units are formed and polymerized to produce isosorbide-containing polymers. The polymers contain at least one difunctional compound that is a diisocyanate or a diisothiocyanate. The isosorbide-containing polymer may be a homopolymer or a copolymer. To form a copolymer, other monomers, which may be non-diisocyanate containing monomers, can be included. For example, other monomers may include dicarboxylic acids, dithiocarboxyclic acids, thiocarboxylic acid, or other difunctional groups. The polymerization conditions are dictated by the type of polymerization method used, such as interfacial polymerization, solution polymerization, or melt polymerization. Any known polymerization technique may be used to produce the polymers of the present invention.

Also provided herein is a method of synthesizing a polyurethane copolymer with an isosorbide adduct of Formula II and/or Formula III, the method comprising:
(a) combining isosorbide or a stereoisomer thereof with a difunctional linker to form a first reaction mixture;
(b) reacting the first reaction mixture under conditions to form an isosorbide adduct;
(c) admixing a difunctional isocyanate linker to the isosorbide adduct to form a second reaction mixture; and
(d) reacting the second reaction mixture under conditions to form a polyurethane copolymer with the isosorbide adduct.

The polyurethane copolymer with the isosorbide adduct may be molded into a desired mold by any known means in the art, including but not limited to, coating the polyurethane copolymer on a wafer to form a film. The polyurethane copolymer may be coated onto the wafer using spin coating, rod coating, or any other known technique in the art.

In some embodiments, the method for preparing a polyurethane copolymer with an isosorbide adduct includes a catalyst in the first reaction mixture. Such catalysts will be dependent on the nature of the identity of the difunctional linkers coupled to the isosorbide in the first reaction step. Acceptable catalysts include, but are not limited to, dibutyl tin oxide, dibutyl tin dilaurate, lithium hydroxide monohydrate, and combinations thereof.

An isosorbide adduct of Formula III prepared by the methods described herein can produce adducts of Formula III with various n values, such that when a single preparation of isosorbide adducts of Formula III are added to a second reaction mixture, the second reaction mixture may comprise adducts of Formula III with differing values for n.

In some embodiments, the method for preparing a polyurethane copolymer with an isosorbide adduct include a catalyst in the second reaction mixture. The identity of catalysts used in the second reaction mixture will depend on the difunctional cyanate linker used. Acceptable catalyst include, but are not limited to, dibutyl tin dilaurate.

In some embodiments, the isosorbide adduct from the first reaction mixture is isolated. Isolation techniques used can include precipitation from non-solvent, chromatography, crystallization, evaporation, or any other known means in the art is isolate the isosorbide adduct formed in the first reaction mixture. In some embodiments, isosorbide adducts of Formula II are purified from the first reaction mixture. In some embodiments, isosorbide adducts of Formula III with specific ranges of n are purified from the first reaction mixture. In some embodiments, the isosorbide adduct is not purified, and the method proceeds with setting up the second reaction mixture.

As discussed above, one or more isosorbide stereoisomers may be used when synthesizing isosorbide adducts of the present invention. Thus, the resulting polymer may contain only isosorbide, isomannide, or isoidide. The resulting polymer may also contain mixtures thereof. Additionally, the difunctional linker used to make the isosorbide adduct may include a dicarboxylic acid, a diester, a dithiol, a cyclic anhydride, a carbonate, or mixtures thereof.

In some embodiments, two or more isosorbide adducts, each with unique Y value, may be added to the second reaction mixture. Additional isosorbide adducts can be synthesized by repeating step (a) of the method described above in a separate reaction vessel for each isosorbide adduct made.

IV. EXAMPLES

The following examples are offered to illustrate, but not limit, the claimed invention.

Example 1. Synthesis of an Isosorbide Polyurethane and Preparation of a Molded Film Thereof A mixture of dried isosorbide (0.002 moles) and H12MDI (0.0021 moles) was added to 25 mL of dried dimethylacetamide in a reaction tube. The reaction tube was sealed with a cap and the resulting mixture was heated and swirled to dissolve the isosorbide. The cap was momentarily removed and 0.005 g of dibutyl tin dilaurate was added to the reaction tube. The solution was degassed with nitrogen for 5 minutes, sealed and placed in a 60° C. oven for about 65 hours, at which time the solution had turned into a soft gel. The tube was then moved to a 90° C. oven for 1 hour and mixed with a spatula. A small additional amount (about 2 mL) of dimethylacetamide was added to produce a thick syrup.

Next, the solid polymer was recovered by precipitation into a non-solvent (for the polymer) to remove dimethylacetamide and unreacted monomers. A portion of the syrup (about 12 mL) was slowly poured into a beaker of rapidly stirred isopropanol (about 150 mL). Upon addition, the syrup formed soft strings which were broken up into particulate matter by the stirring. The stirring was stopped, and the particulate matter was allowed to harden in the isopropanol solvent. Once the particulate matter hardened, the isopropanol was decanted, fresh isopropanol (about 150 mL) was added to the beaker, and another small portion of the syrup was added (with stirring during the addition). This process was repeated until all the syrup was added to the beaker. The hardened particulate matter in the isopropanol solvent after the final addition of syrup was left to stand overnight in a covered beaker to extract remaining monomer and high boiling solvent. The extracted polymer was recovered by filtration and dried at 65° C. followed by 90° C.

Next, the extracted polymer was spin coated to form a polymer film. First, a small quantity of the dried polymer was dissolved in a mixture of chloroform and benzyl alcohol (80:20). A silicon wafer was cleaned and placed on a low speed spin coater. While running at low speed, 1 ml of the polymer solution was syringed rapidly onto the center of the wafer. After 3 seconds the speed was increased and then turned off. The coated wafer was partially covered with a loose aluminum pan and placed in a 90° C. forced air oven to dry.

After polymer film formation was complete, the wafer was dried in a 120° C. oven for 30 minutes. After drying, a portion of the polymer film was submitted for optical measurements.

The dried film was then converted to a molded film. Three grams of dry polymer was pressed between a silicone/glass release sheet at 149° C. The initial film was cut into four parts, which were stacked and re-pressed to yield a thin clear film about 0.010 inches thick.

Figure 2:
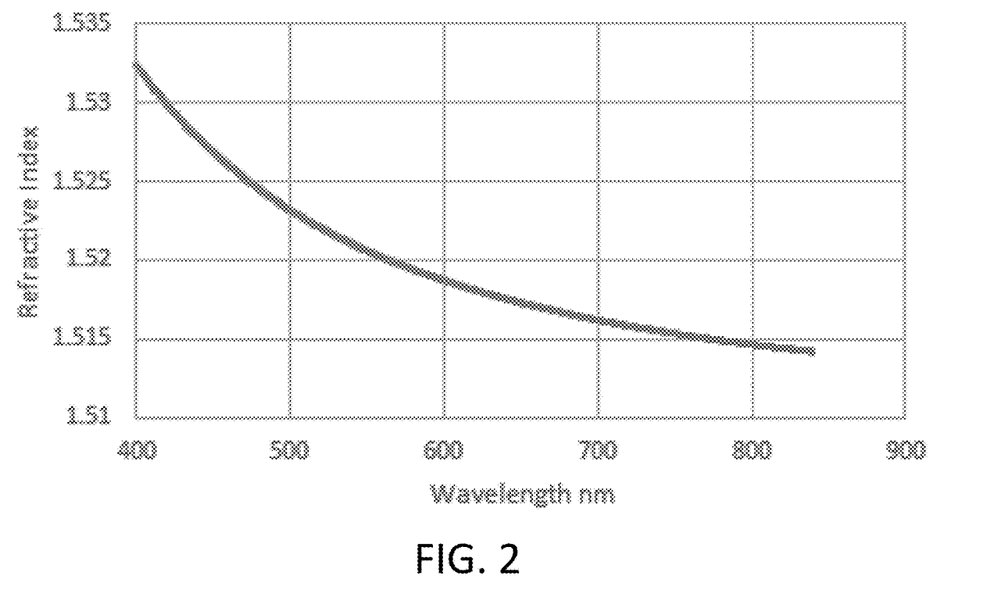
FIG. 2 shows a spectral curve of an isosorbide polyurethane measuring the refractive index in accordance with an embodiment of the present invention.

FIG. 2 illustrates a spectral curve of the dried polymer film. The spectral curve reports the refractive index of the dried polymer film at each wavelength. From this data, the Abbe value was determined to be 75.117. The Abbe value was calculated as shown in Table 1.

TABLE 1

| Polymer Film Abbe Value | | | | | |
|---|---|---|---|---|---|
| Wavelength | | | | | |
| 589.3 nm | D | 1.5191 | Abbe = | 75.117 |
| 486.1 nm | F | 1.5241 | | |
| 656.3 nm | C | 1.5172 | | |

Figure 3:
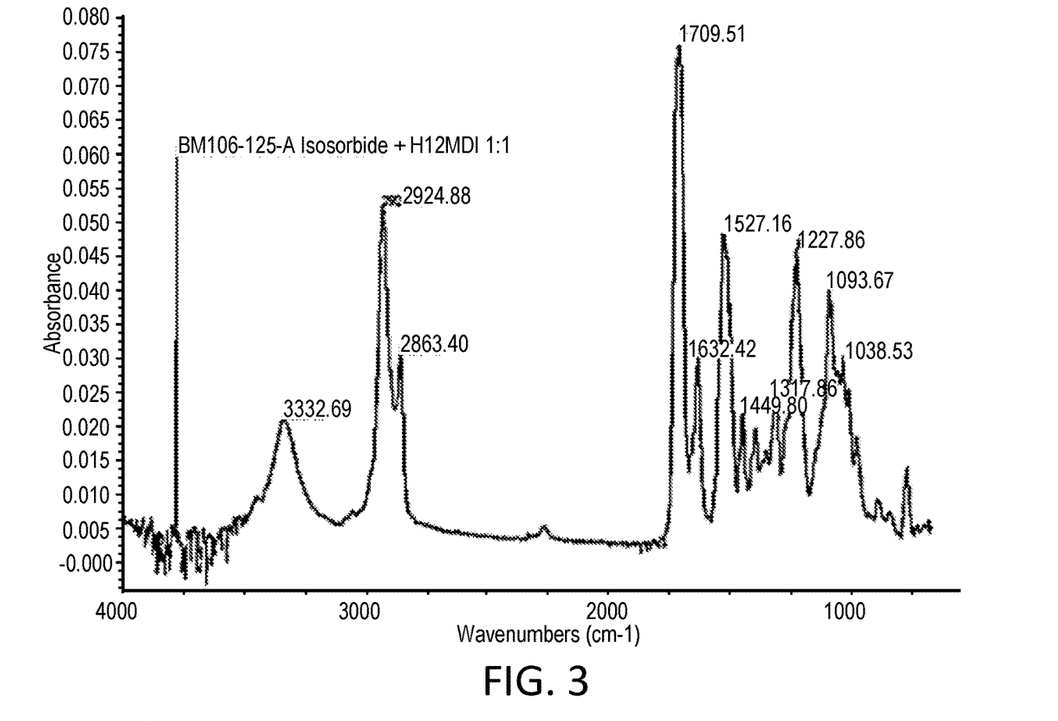
FIG. 3 shows a Fourier transform infrared spectroscopy (FTIR) plot of an isosorbide polyurethane in accordance with an embodiment of the present invention.
Figure 4:
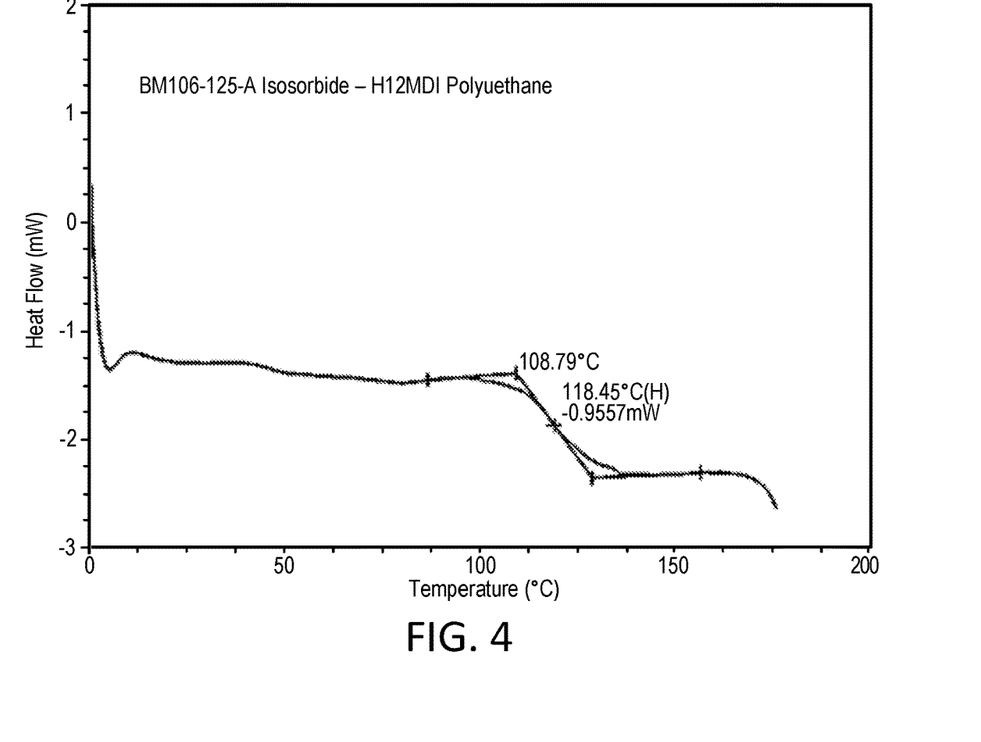
FIG. 4 shows a differential scanning isotherm plot of an isosorbide polyurethane in accordance with an embodiment of the present invention.

A representative Fourier transform infrared spectrosopy plot and differential scanning isotherm plot of polymer films using this method are shown in FIG. 3 and FIG. 4, respectively; differential scanning calorimetry analysis of polymer film indicated a glass transition temperature (Tg) of 117° C. The polymer films were ductile (not brittle).

Example 2. Synthesis of an Isosorbide Adduct with Succinic Anhydride and Preparation of a Polymer and Film Thereof Isosorbide (3 mole equivalents) was combined with one equivalent of succinic anhydride in a 100-ml round bottomed flask and heated with stirring at 150° C. for 1 hour to yield a viscous mixture of isosorbide and the 2:1 adduct of isosorbide with succinic anhydride. Dried dimethyl formamide was added to this mixture, yielding a solution of 20% solids. Two mole equivalents of H12MDI was added to the reaction mixture. After addition of the H12MDI, the solution was degassed with a stream of nitrogen for 5 minutes, and a cap was added to seal the round bottom flask. The cap was momentarily removed, 0.010 g of dibutyl tin dilaurate was added to the flask, and the flask was then heated at 90° C. for 8 hours. About 20 mL of the resulting viscous solution was cast into an aluminum tray by pouring the reaction mixture directly onto the aluminum tray. The solution was then dried for 4 hours at 60° C. followed by 10 hours at 110° C. in a forced air oven. This resulted in a highly clear transparent film.

Example 3. Synthesis of an Isosorbide Adduct with Dimethyl 3,3'-disulfanediyldipropanoate and Preparation of a Polymer and Film Thereof Isosorbide (3 mole equivalents), dimethyl 3,3'-dithiodipropionate (one mole equivalent), and 0.05% dibutyl tin oxide was sequentially added to a 100-mL round bottomed flask. The resulting mixture was stirred and heated at 90° C. for 4 hours to yield a viscous mixture of isosorbide and the 2:1 adduct of isosorbide with 3,3'-dithiodipropionate. Dried dimethylformamide was added to this mixture, yielding a solution of 20% solids. Next, two equivalents of H12MDI was added to the reaction mixture. After addition of the H12MDI, the solution was degassed with a stream of nitrogen for 5 minutes, and a cap was added to seal the round bottom flask. The cap was momentarily removed, 0.010 g of dibutyl tin dilaurate was added to the flask, and the flask was then heated at 90° C. for 8 hours. About 20 mL of the resulting viscous solution was cast into an aluminum tray. The aluminum tray was dried for 4 hours at 60° C. followed by 10 hours at 110° C. in a forced air oven. This resulted in a highly clear transparent film.

Example 4. Synthesis an Isosorbide Copolymer and Preparation of a Molded Film Thereof A mixture of dried isosorbide (0.002 moles), H12MDI (0.00105 moles), and hexamethylene diisocyanate (0.00105 moles) was added to 25 mL of dried dimethylacetamide in a reaction tube. The reaction tube was sealed with a cap and the resulting mixture was heated and swirled to dissolve the isosorbide. The cap was momentarily removed and 0.005 g of dibutyl tin dilaurate was added to the reaction tube. The solution was degassed with nitrogen for 5 minutes, sealed and placed in a 60° C. oven for about 65 hours, after which time the solution was a soft gel. The tube was then moved to a 90° C. oven for 1 hour and mixed with a spatula. A small additional amount (about 2 mL) of dimethylacetamide was added to produce a thick syrup.

Next, the solid polymer was recovered and extracted to remove dimethylacetamide and unreacted monomers. A portion of the syrup (about 12 mL) was slowly poured into a beaker of rapidly stirring isopropanol (about 150 mL). Upon addition, the syrup formed soft strings which were broken up into particulate matter by the stirring. The stirring was stopped, and the particulate matter was allowed to harden in the isopropanol solvent. Once the particulate matter hardened, the isopropanol was decanted, fresh isopropanol (about 150 mL) was added to the beaker, and another small portion of the syrup was added (stirring is recommended when the syrup is being added to the beaker). This process was repeated until all the syrup had been added to the beaker. The hardened particulate matter in the isopropanol solvent after the final addition of syrup was left to stand for an extended time (e.g. overnight) in a covered beaker to extract unreacted monomer and dimethylacetamide. The extracted polymer was recovered by filtration and dried at 65° C. followed by 90° C.

Next, the extracted polymer was spin coated to form a film. First, a small quantity of the dried polymer was dissolved in a mixture of chloroform and benzyl alcohol (80:20). A silicon wafer was cleaned and placed on a low speed spin coater. While running at low speed, about 1 ml of the polymer solution was syringed rapidly onto the center of the wafer. After about 3 seconds the speed was increased and then the spin coater was turned off. The coated wafer was partially covered with a loose aluminum pan and placed in a 90° C. forced air oven to dry.

After film formation was complete, the wafer was dried in a 120° C. oven for 30 minutes.

Next, the dried film was converted to a molded film. Three grams of dry polymer was pressed between a silicone/glass release sheet at 149° C. The initial film was cut into four parts, which were stacked and re-pressed to yield a thin clear film about 0.010 inches thick. The resulting molded film was highly transparent.

Example 5. Synthesis of an Isosorbide Adduct with Carbonate and Preparation of a Polymer and Film Thereof Four mole equivalents of isosorbide were combined with 1 mole equivalent of diphenyl carbonate and 0.02 mole equivalent of lithium hydroxide monohydrate in a round bottomed flask. The mixture was heated at 100° C. for 2 hours. After 2 hours, the pressure in the round bottom flask was reduced to about 0.05 bar and the reaction was allowed to proceed at 100° C. for an additional 3 hours. The reduced pressure removed the phenol generated in the reaction. After 3 hours, diethyl ether was added to the reaction mixture, and the solution was extracted three times with water, followed by an extraction with saturated sodium chloride. The extracted reaction solution was dried over sodium sulfate and filtered, and the volume was then reduced under vacuum. The reduced volume was added to boiling ethyl acetate and allowed to crystallize. The crystalline material comprising isosorbide carbonate was filtered and dried.

One mole equivalent of the isosorbide carbonate was reacted with 1.05 mole equivalents of H12MDI in dimethylacetamide with 0.05% of dibutyl tin dilaurate in a round bottomed flask for 8 hours at 90° C. The resulting viscous solution is extracted by pouring the viscous solution into rapidly stirred ethanol to form an extraction mixture. The extraction mixture was allowed to incubate for 3 hours. After 3 hours, the extraction mixture was filtered using vacuum filtration and dried under vacuum at 80° C. for 12 hours. The resulting polymer was highly transparent.

Example 6. Synthesis of an Isosorbide Polyurethane and Preparation of a Molded Film Thereof A mixture of dried isosorbide (0.004 moles) recrystallized from methanol, and H12MDI (0.0043 moles), was added to 5 mL of dried dimethylacetamide in a reaction tube. The reaction tube was sealed with a cap and the resulting mixture was heated and swirled to dissolve the isosorbide. The cap was momentarily removed and 0.05 g of dibutyl tin dilaurate was added to the reaction tube. The solution was purged with argon for 5 minutes, sealed and placed in a 60° C. oven for about 65 hours, after which time the solution was a soft gel. The tube was then moved to a 90° C. oven for 4 hours and mixed with a spatula.

The viscous solution was then slowly poured into a beaker of rapidly stirring methanol. Upon addition, the syrup formed soft strings which were broken up into particulate matter by the stirring. The formed strings of polymer were filtered and dried before being dissolved again in dimethylacetamide. This polymer solution was then poured into vigorously stirring methanol to reprecipitate the polymer. The resulting white polymer was recovered by filtration and dried at 80° C.

Next, the extracted polymer was spin coated to form a film. First, a small quantity of the dried polymer was dissolved in a mixture of chloroform and benzyl alcohol (80:20). A silicon wafer was cleaned and placed on a low speed spin coater. While running at low speed, about 0.5 ml of the polymer solution was syringed rapidly onto the center of the wafer. After about 3 seconds the speed was increased and then the spin coater was turned off. The coated wafer was partially covered with a loose aluminum pan and placed in a 90° C. forced air oven to dry. The resulting thin film had a refractive index of 1.5316 and an Abbe value of 69.8.

Although the foregoing invention has been described in some detail by way of illustration and example for purpose of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A polyurethane copolymer comprising a repeating unit of Formula I:

(I)

wherein:
ISO in each repeating unit is independently selected from isosorbide or a stereoisomer thereof; and
X in each repeating unit is an independently selected difunctional linker,
wherein the difunctional linker is a diisothiocyanate, wherein the diisothiocyanate is selected from the group consisting of 4, 4'-methylenebis(cyclohexylisothiocyanate), methylenebis(phenyl isothiocyanate), hexamethylene diisothiocyanate, isophorone diisothiocyanate, cyclohexane diisothiocyanate, butane diisothiocyanate, and 1,3-bis(isothiocyanatomethyl) cyclohexane, and
wherein the polyurethane copolymer has a refractive index of at least about 1.5 and an Abbe value of at least about 50.

2. The polyurethane copolymer of claim 1, wherein the stereoisomer is selected from the group consisting of isomannide and isoidide.

3. The polyurethane copolymer of claim 1, wherein the polyurethane copolymer has a light transmittance of at least about 80%.

4. The polyurethane copolymer of claim 1, wherein the polyurethane copolymer has a yellow index of lower than about 10.

5. An isosorbide adduct of Formula II:

(II)

wherein:
ISO is independently selected from isosorbide or a stereoisomer thereof; and
Y is a difunctional linker selected from the group of a dithiocarboxylic acid, a carbonate, and a thiocarbonate, a difunctional compound comprising carboxylic acid and thiocarboxylic acid functional groups; wherein the dithiocarboxylic acid is selected from the group consisting of succinthioic acid, 3,3'-disulfanediyldipropanthioic acid, 2,2'-disulfanediyldiethanthioic acid, and 4,4'-disulfanediyldibutanthioic acid.

6. The isosorbide adduct of claim 5, wherein the stereoisomer is selected from the group consisting of isomannide and isoidide.

7. The isosorbide adduct of claim 5, wherein the difunctional compound is selected from the group consisting of 4-((3-thiocarboxypropyl)disulfanyl)butanoic acid, 3-((2-thiocarboxyethyl)disulfanyl)propionic acid, 2-((thiocarboxymethyl)disulfanyl)acetic acid, 4-hydroxy-4-thioxobutanoic acid.

8. The isosorbide adduct of claim 5, wherein the carbonate is diphenyl carbonate.

9. A polyurethane copolymer comprising:
one or more isosorbide adducts of claim 5; and
one or more diisothiocyanate linker, wherein the diisothiocyanate is selected from the group consisting of 4, 4'-methylenebis(cyclohexylisothiocyanate), methylenebis(phenyl isothiocyanate), hexamethylene diisothiocyanate, isophorone diisothiocyanate, cyclohexane diisothiocyanate, butane diisothiocyanate, 1,3-bis(isothiocyanatomethyl) cyclohexane, and combinations thereof.

10. The polyurethane copolymer of claim 9, wherein the polyurethane copolymer has a refractive index of at least about 1.5.

11. The polyurethane copolymer of claim 9, wherein the polyurethane copolymer has an Abbe value of at least about 50.

12. The polyurethane copolymer of claim 9, wherein the polyurethane copolymer has a light transmittance of at least about 80%.

13. The polyurethane copolymer of claim 9, wherein the polyurethane copolymer has a yellow index of lower than about 10.

* * * * *